United States Patent
Pail

(10) Patent No.: US 6,561,987 B2
(45) Date of Patent: May 13, 2003

(54) APPARATUS AND METHODS FOR INDICATING RESPIRATORY PHASES TO IMPROVE SPEECH/BREATHING SYNCHRONIZATION

(76) Inventor: Opher Pail, 625 Main St., Apt. 1433, New York, NY (US) 10044

( * ) Notice: Subject to any disclaimer, the term of this patent is extended or adjusted under 35 U.S.C. 154(b) by 00 days.

(21) Appl. No.: 09/828,815

(22) Filed: Apr. 10, 2001

(65) Prior Publication Data

US 2002/0123692 A1 Sep. 5, 2002

Related U.S. Application Data

(60) Provisional application No. 60/272,503, filed on Mar. 2, 2001.

(51) Int. Cl.$^7$ .................................................. A61B 5/08
(52) U.S. Cl. ....................................... 600/534; 600/529
(58) Field of Search ................................. 600/529, 534

(56) References Cited

U.S. PATENT DOCUMENTS

| | | | |
|---|---|---|---|
| 3,672,352 A | * 6/1972 | Summers | ..................... 600/476 |
| 3,782,368 A | 1/1974 | Rebold | |
| 4,169,462 A | 10/1979 | Strubé | |
| 4,248,242 A | * 2/1981 | Tamm | ......................... 600/491 |
| 4,579,124 A | 4/1986 | Jentges | |
| 4,694,839 A | 9/1987 | Timme | |
| 4,777,962 A | 10/1988 | Watson et al. | |
| 4,803,997 A | 2/1989 | Bowman | |
| 4,846,157 A | * 7/1989 | Sears | ......................... 601/71 |
| 4,889,131 A | 12/1989 | Salem et al. | |
| 4,909,260 A | 3/1990 | Salem et al. | |
| 4,960,118 A | * 10/1990 | Pennock | ..................... 600/534 |
| 4,982,738 A | 1/1991 | Griebel | |
| 5,107,855 A | 4/1992 | Harrington et al. | |
| 5,166,463 A | 11/1992 | Weber | |
| 5,274,548 A | 12/1993 | Bernard et al. | |
| 5,277,194 A | 1/1994 | Hosterman et al. | |
| 5,295,490 A | 3/1994 | Dodakian | |
| 5,304,984 A | 4/1994 | Roldan | |
| 5,395,301 A | * 3/1995 | Russek | ......................... 601/41 |
| 5,400,012 A | * 3/1995 | Walton | ..................... 340/573.1 |
| 5,520,176 A | 5/1996 | Cohen | |
| 5,540,733 A | 7/1996 | Testerman et al. | |
| 5,555,891 A | 9/1996 | Eisenfeld | |
| 5,730,145 A | * 3/1998 | Defares et al. | ............. 600/595 |
| 5,765,135 A | 6/1998 | Friedman et al. | |
| 5,794,203 A | 8/1998 | Kehoe | |
| 6,162,183 A | * 12/2000 | Hoover | ....................... 600/534 |

FOREIGN PATENT DOCUMENTS

| | | | | |
|---|---|---|---|---|
| GB | 1 588 217 | | 8/1977 | |
| JP | 06063031 A | * | 3/1994 | ............ A61B/5/08 |

* cited by examiner

Primary Examiner—Robert L. Nasser
Assistant Examiner—Patricia C. Mallari

(57) ABSTRACT

An indicating apparatus includes a strap for being worn by a user and having a variable condition that changes during the inspiration and expiration phases, respectively, of a respiratory cycle of the user. The strap has a sensor that senses the variable condition and generates electrical output indicative of the variable condition during the inspiration and expiration phases. A signaling device of the indicating apparatus produces a tactile vocalization signal in response to the electrical output that is generated during the expiration phase and produces a tactile pause signal in response to the electrical output that is generated during the inspiration phase. The vocalization and pause signals prompt the user, over a plurality of respiratory cycles, to properly synchronize speaking with the expiration phases and pauses in speaking with the inspiration phases. A method of indicating respiratory phases involves sensing a variable condition of a strap worn by a user, generating electrical output indicative of the variable condition during inspiration and expiration, and producing tactile signals for the user indicative of inspiration and expiration, respectively.

34 Claims, 5 Drawing Sheets

APPARATUS AND METHODS FOR INDICATING RESPIRATORY PHASES TO IMPROVE SPEECH/BREATHING SYNCHRONIZATION

CROSS-REFERENCE TO RELATED PATENT APPLICATION

This application claims priority from prior U.S. provisional patent application Ser No. 60/272,503 filed Mar. 2, 2001.

BACKGROUND OF THE INVENTION

1. Field of the Invention

The present invention relates generally to apparatus and methods for improving speech through proper synchronization of speech and breathing. More particularly, the present invention relates to apparatus and methods for indicating respiratory phases in an individual so that speech may be self-synchronized with respiration.

2. Brief Description of the Related Art

Respiration or breathing occurs as respiratory or breathing cycles, each lasting about four seconds and having an inspiration or inhalation phase followed by an expiration or exhalation phase. In the inspiration phase, the respiratory muscles of the chest and abdomen expand, allowing inspiration or inhalation of air through the anatomical airway and into the lungs. Conversely, the respiratory muscles contract in the expiration phase, allowing expiration or exhalation of air from the lungs and the anatomical airway.

It is essential for speech fluency that speech be properly and precisely synchronized with respiration. Speech production occurs as speech cycles, each beginning with a relatively rapid inspiration or inhalation in the inspiration phase of the respiratory cycle. As the respiratory muscles thereafter contract in the expiration phase of the respiratory cycle, air is pushed out through the vocal folds, thereby generating voice, and through the articulating structures of the mouth, thereby generating sounds. The speech cycle ends when no more air is being exhaled, and a new speech cycle begins with another relatively rapid inspiration in the inspiration phase, during which a pause in speaking occurs. Fluent speech requires constant airflow out while speaking or vocalizing and short inspirations perfectly timed during pauses in speaking. Accordingly, the speech cycle must be synchronized with the respiratory cycle in that pauses in speaking or vocalization must be synchronized with the inspiration phase, and speaking must be synchronized with the expiration phase.

A great number of people are deficient in normal speech production and experience impaired synchrony of speech and respiration due to clinical disorders or disease. Improper synchronization between speech and breathing are affiliated with speech dysfluencies and speech impediments such as stuttering. In the U.S. alone, there are an estimated 2.4 million adults who stutter. Various other speech problems, such as cerebral palsy speech and chronic voice disorders, are not uncommon. Speech production and fluency for individuals with defective or impaired speech may be improved by improving speech/respiration synchronization. Although patients can be taught speech/respiration synchrony in a clinical setting, it is difficult for the patients to implement the teachings once they leave the clinical environment. There are no inconspicuous, portable devices for continuously and effectively indicating respiratory phases in individuals to allow self-synchronization of speech and respiration, particularly in a non-clinical environment.

Various devices have been proposed to monitor or detect breathing interruptions or cessations, as represented by U.S. Pat. No. 5,555,891 to Eisenfeld, No. 5,540,733 to Testerman, No. 5,295,490 to Dodakian, No. 5,277,194 to Hosterman et al., No. 5,107,855 to Harrington et al., Nos. 4,909,260 and 4,889,131 to Salem et al., and No. 4,694,839 to Timme. The Dodakian and Salem et al. patents disclose the use of belts to assist monitoring. U.S. Pat. No. 3,782,368 to Reibold discloses a belt with a sensor for measuring breathing frequency. None of the foregoing patents is concerned with indicating specific inspiration and expiration respiratory phases of breathing. A speech training system for training and improving the coordination between respiration and voice production is disclosed in U.S. Pat. No. 5,765,135 to Friedman et al. The system requires a microphone and respiratory sensors connected to video display and voice output units for simultaneously displaying voice and breathing motion patterns. Since the user must be connected to the video display, the system is not portable and is not amenable to being used by an individual in a non-clinical setting, must less during normal routine activities.

SUMMARY OF THE INVENTION

It is a primary object of the present invention to overcome the aforementioned disadvantages of the prior art in the area of speech/breathing synchronization.

Another object of the present invention is to continuously indicate respiratory phases in individuals in non-clinical environments.

A further object of the present invention is to continuously indicate respiratory phases in an individual via a portable indicating apparatus capable of being inconspicuously worn by the individual. An additional object of the present invention is to continuously communicate tactile signals to an individual indicative of respiratory phases being experienced by the individual.

It is also an object of the present invention to utilize the position of the respiratory muscles in an individual during respiration to obtain an indication of respiratory phases.

The present invention has as a further object to use inaudible, tactile signals to stimulate an individual to speak in synchrony with the expiration phase of respiration and to pause between speaking in synchrony with the inspiration phase of respiration.

The advantages of the present invention are that the apparatus and methods are applicable to a wide range of speech impediments and disorders, continuous and instantaneous feedback of breath stream dynamics may be provided to users, users of the apparatus and methods do not need to be connected or "hooked up" to any cumbersome equipment, the apparatus and methods can be used by individuals while engaged in normal, routine activities, the duration of each respiratory phase is apparent to users so that respiration rate may be self-controlled to maintain optimal conditions, and the apparatus and methods are beneficial for use in other applications or areas, such as general relaxation.

These and other objects, advantages and benefits are realized with the present invention as generally characterized in an indicating apparatus comprising a strap for being worn by a user, typically around the chest or abdomen. The strap has a variable condition that changes in response to expansion of the user's respiratory muscles as air is inhaled during the inspiration phase of a respiratory cycle and contraction of the user's respiratory muscles as air is exhaled during the expiration phase of the respiratory cycle. A sensor of the indicating apparatus is carried by or forms part of the strap and is adapted to sense or detect the variable condition of the strap during the respiratory cycle. The sensor generates digital or linear electrical output indicative of the sensed variable condition. If a linear electrical output is generated, a processor of the indicating apparatus processes the electrical output of the sensor to determine whether the user is inhaling or exhaling. The processor, which is carried by the strap, generates a first command signal when it determines that the user is inhaling and generates a second command signal when it determines that the user is exhaling. If a digital electrical output is generated, the first and second command signals can be obtained therefrom without the need for a processor. The first and second command signals are used to operate one or more signaling devices of the indicating apparatus. The one or more signaling devices, which are carried by the strap, are operable to produce a tactile pause signal when the first command signal is generated and to produce a tactile vocalization signal when the second command signal is generated. Accordingly, the tactile pause signal is produced while the user is inhaling, and the tactile vocalization signal is produced while the user is exhaling. The vocalization signal serves as a prompt to the user to speak in synchrony with the expiration phase. The pause signal serves as a prompt to the user to pause from speaking in synchrony with the inspiration phase. Over a plurality of respiratory cycles, the indicating apparatus assists the user in properly synchronizing speaking with the expiration phases and pauses between speaking with the inspiration phases so as to improve speech fluency.

A method according to the present invention of indicating respiratory phases in a user is generally characterized in the steps of sensing a variable condition of a strap that is worn by a user as the variable condition changes in response to expansion and contraction of the respiratory muscles of the user during inhalation and exhalation, respectively; determining whether the user is inhaling or exhaling from the sensed variable condition; and producing a first tactile signal indicative of inspiration in response to a determination that the user is inhaling or a second tactile signal, tactilely distinguishable from the first signal, indicative of expiration in response to a determination that the user is exhaling.

A method according to the present invention of self-synchronizing speech with respiration is generally characterized in the steps of wearing a stretchable strap of an indicating apparatus so that the strap linearly expands in response to expansion of the respiratory muscles during the inspiration phase of a respiratory cycle and linearly contracts in response to contraction of the respiratory muscles during the expiration phase of the respiratory cycle; perceiving a tactile vocalization signal produced by the indicating apparatus while the strap is linearly contracting; speaking while the tactile vocalization signal is perceived; perceiving a tactile pause signal produced by the indicating apparatus while the strap is linearly expanding; and inhaling air and pausing from speaking while the tactile pause signal is perceived. When repeated over a plurality of respiratory cycles, the user is able to synchronize speaking with the expiration phases and to synchronize inhalation and pauses in speaking with the inspiration phases of the respiratory cycles.

Other objects and advantages of the present invention will become apparent from the following description of the preferred embodiments taken in conjunction with the accompanying drawings, wherein like parts in each of the several figures are identified by the same reference numbers.

DESCRIPTION OF THE PREFERRED EMBODIMENTS

Figure 1:
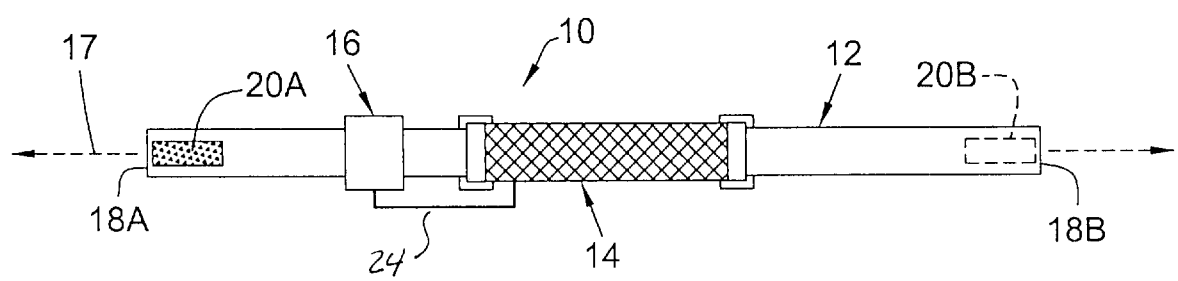
FIG. 1 is a front plan view of an indicating apparatus according to the present invention.
Figure 2:
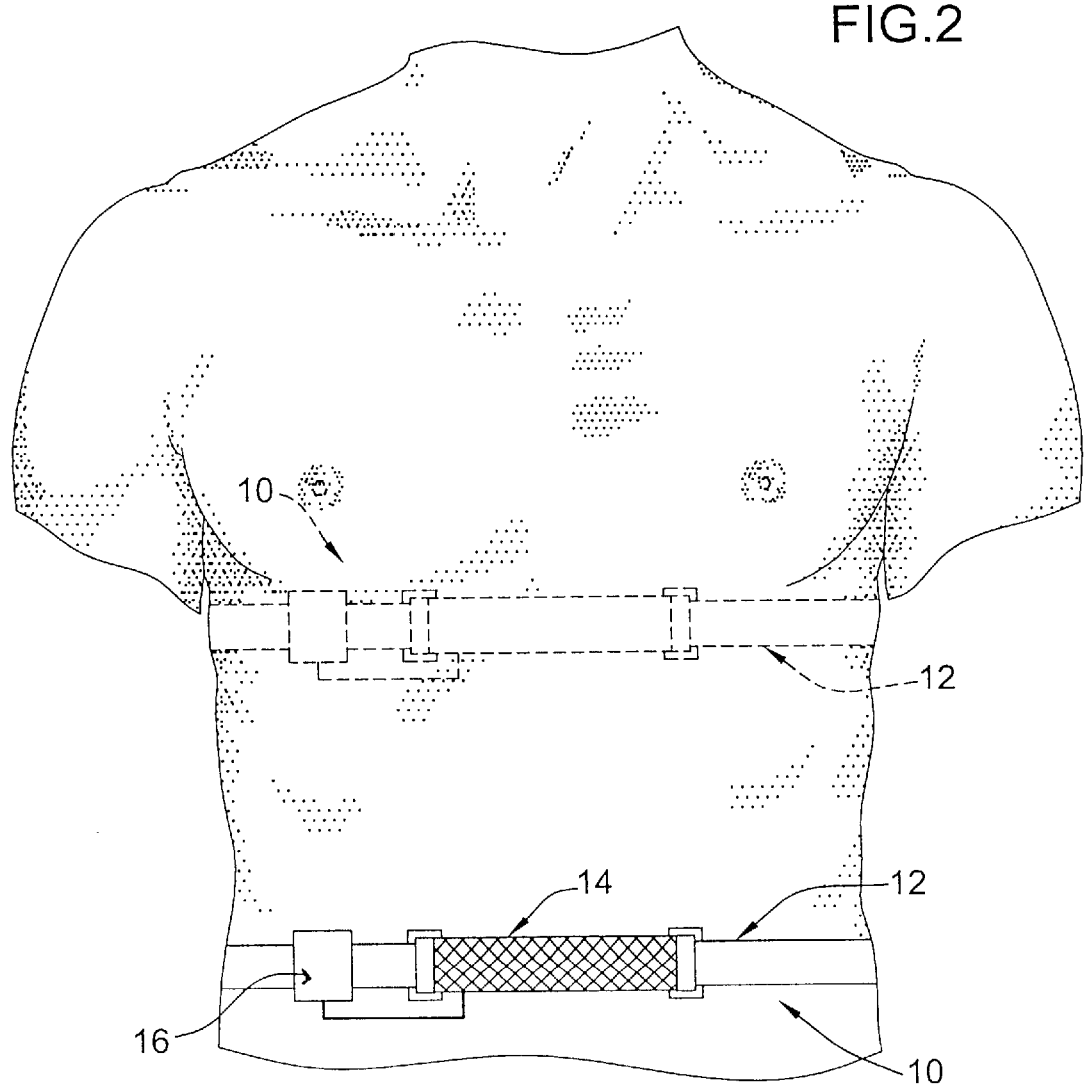
FIG. 2 is a broken front view showing the indicating apparatus worn by a user.
Figure 3:
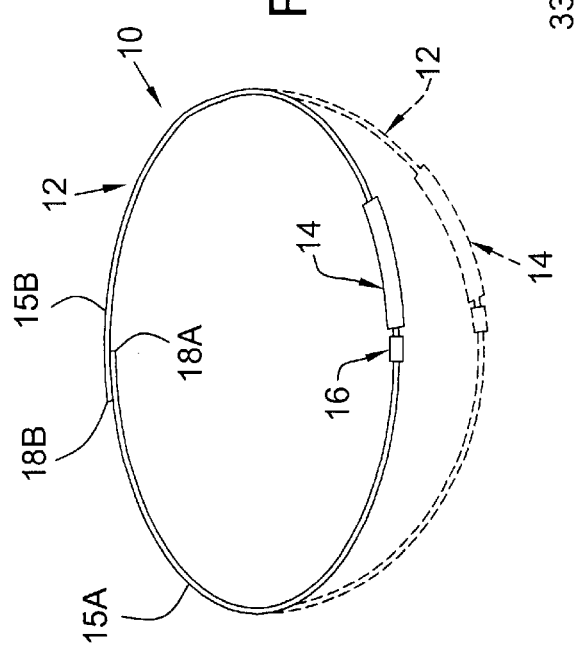
FIG. 3 is a top view illustrating contracted and expanded conditions for the indicating apparatus during a respiratory cycle of the user.

A portable indicating apparatus 10 for indicating respiratory phases in an individual, user or patient is illustrated in FIGS. 1–3. The indicating apparatus 10 includes a strap or belt 12, a sensor 14 carried by or forming part of strap 12, and a control unit 16 mounted on strap 12. Strap 12 is linearly expandable and contractible. As such, the entire strap or at least a segment thereof is made of elastic or stretchable material. The strap 12 is shown in FIG. 1 in a relaxed or unstretched condition wherein the strap is not stretched, elongated or lengthened in the direction of its longitudinal axis 17. Strap 12 has opposing free ends 18A and 18B provided with releaseable fasteners 20A and 20B, respectively. Strap 12 has a variable length between the free ends 18A and 18B sufficient to snugly encircle the chest or abdomen of individuals of various physical sizes with the free ends 18A and 18B fastened via the fasteners 20A and 20B as shown in FIGS. 2 and 3. The fasteners 20A and 20B can be designed in various ways to releaseably secure strap 12 on an individual in an adjustable manner. In the case of strap 12, fasteners 20A and 20B are formed by respective strips of complementary hook and loop material such as Velcro. The fastener 20A is disposed along a front face of strap 12, and the fastener 20B is disposed along a back face of strap 12. As shown in FIG. 3, the ends 18A and 18B are overlapped to lockingly engage the fasteners 20A and 20B, which are selectively released or disengaged merely by pulling the ends 18A and 18B apart. The fasteners 20A and 20B have a length to permit sufficient variance in overlap of ends 18A and 18B so as to accommodate the chests or abdomens of individuals of various sizes and to allow desired tension adjustments.

The anatomical location at which strap 12 is secured on an individual, patient or user is selected such that movements of the individual's respiratory muscles during respiration are translated into linear movements of strap 12. Positioning of strap 12 around the individual's abdomen, as shown in solid lines in FIG. 2, or chest, as shown in dotted lines in FIG. 2, results in linear expansion and contraction of strap 12 in response to expansion and contraction, respectively, of the abdomen or chest during respiration. As shown in solid lines in FIG. 3, strap 12 is in a first or contracted condition when the individual's respiratory muscles are contracted just prior to the beginning of a respiratory cycle. The respiratory cycle begins with the inspiration or inhalation phase, during which the respiratory muscles expand as air is inhaled by the individual. Expansion of the chest and abdomen during the inspiration phase causes linear expansion, elongation, lengthening or stretching of strap 12 in the axial or longitudinal direction, i.e. along longitudinal axis 17. At the end of the inspiration phase, strap 12 is in a second or expanded condition, shown in dotted lines in FIG. 3, wherein the length of the strap is greater than it was in the contracted condition. The expiration or exhalation phase of the respiratory cycle ensues, with contraction of the respiratory muscles as air is expired or exhaled. Contraction of the chest and abdomen during the expiration phase causes contraction, retraction or shortening of strap 12 in the axial or longitudinal direction as it is moved from the expanded condition toward the contracted condition. At the end of the expiration phase, i.e. the end of the respiratory cycle, strap 12 will be in a contracted condition, wherein the length of the strap is less than it was in the previous expanded condition. Accordingly, the variable length of strap 12 represents a variable or changeable condition that varies or changes in response to expansion and contraction of the user's respiratory muscles during inhalation and exhalation, respectively. For each respiratory cycle, the strap 12 is moved in a first linear direction during the inspiration phase and is moved in a second linear direction during the expiration phase.

Depending on construction, strap 12 in the contracted condition may or may not be linearly expanded, elongated, stretched or lengthened to some extent from its relaxed condition. Typically, the strap in the contracted condition will be linearly expanded, lengthened, stretched or elongated to some extent from its relaxed condition due to initial tension created in the strap to achieve a snug fit on the individual or user. The creation of some initial tension in the strap is desirable to ensure a secure fit on the user and to enhance the responsiveness of the strap to expansion and contraction of the respiratory muscles. Accordingly, as used herein, "first condition" and "contracted condition" refer to the variable length, linear condition, or some other changeable or variable condition of strap 12 at the beginning of a respiratory cycle, i.e. at the end of the expiration phase of the previous respiratory cycle, regardless of whether the strap is or is not linearly expanded, stretched, elongated or lengthened from its relaxed condition. Similarly, as used herein, "second condition" and "expanded condition" refer to the variable length, linear condition, or some other changeable or variable condition of strap 12 at the beginning of the expiration phase of the respiratory cycle.

Since the volume of air that is exhaled is not the same for each respiratory cycle, it should be appreciated that the length of strap 12 in the first or contracted condition will not be the same for each expiration phase. For example, the length of strap 12 in the first or contracted condition ranges from a maximum contracted length when a minimum volume of air is exhaled to a minimum contracted length when a maximum volume of air is exhaled. The volume of air that is inhaled is also not the same for each respiratory cycle and, therefore, it should be appreciated that the length of strap 12 in the second or expanded condition will not be the same for each inspiration phase. For instance, the length of strap 12 in the second or expanded condition ranges from a maximum expanded length when a maximum volume of air is inhaled to a minimum expanded length when a minimum volume of air is inhaled. The maximum and minimum volumes of exhaled and inhaled air will typically vary for different individuals as well as varying over a plurality of respiratory cycles for a specific individual depending on various factors such as respiration rate and exertion.

When the strap 12 is in the expanded condition, tension in the strap is increased or is greater than the tension in the strap in the contracted condition since the strap is linearly expanded, elongated, stretched or lengthened in the axial direction. Conversely, tension in the strap in the contracted condition is decreased or is less than the tension in the strap in the expanded condition due to linear or axial contraction, retraction or shortening of the strap. The positive (increase) and negative (decrease) changes in tension in the strap thusly correspond to the positive (expansion) and negative (contraction) linear or length changes that the strap undergoes. Accordingly, strap 12 has a variable tension representing another variable or changeable condition that varies or changes in response to expansion and contraction of the user's respiratory muscles during respiration.

Sensor 14 is carried by or forms part of strap 12 and, in the case of indicating apparatus 10, the sensor forms a length segment of strap 12. Opposing ends of the sensor 14 are connected to elastic or stretchable strap segments or bands, 15A and 15B, respectively, such that the strap comprises three length segments defined by the sensor 14 and the strap segments 15A and 15B, respectively, as shown in FIG. 3. Sensor 14 is disposed at any suitable location to sense the variable length, variable tension, or other variable or changeable condition of strap 12 being utilized to determine whether the strap is expanding or contracting. It should be appreciated that the sensor could be disposed within the strap or on an external face or surface of the strap. Sensor 14 can be designed in various ways to detect or sense the variable length, variable tension, or other variable or changeable condition of strap 12 as the variable condition changes during the user's respiration, and to translate the detected or sensed variable length, variable tension, or other variable or changeable condition into electrical output. For example, sensor 14 may detect, measure or sense actual length, changes in length, actual tension and/or changes in tension in strap 12 as it is linearly expanded and contracted.

Sensor 14 may be a piezoelectric film element, a spring-loaded mechanism connected to an adjustable resistor or any other electrical output generating device, a resistive flexible member, or any other sensing device capable of sensing a changeable or variable condition of strap 12 and providing an electrical output, such as a linear electrical output (LEO) or a digital electrical output (DEO) representative of the changeable or variable condition during respiration. The linear electrical output of sensor 14 may be in ohms, voltage, amps or other forms. A representative piezoelectric film element sensor that generates linear electrical output (LEO) may react to linear changes in strap 12 to provide a linear electrical output (LEO) proportional to or reflective of the linear condition of strap 12. The linear electrical output will range from a maximum linear electrical output corresponding to the maximum expanded length of strap 12 in the expanded condition to a minimum linear electrical output corresponding to the minimum contracted length of strap 12 in the contracted condition. A representative piezoelectric film element sensor that generates digital electrical output may bend in a first direction, for example inward, generating electrical current in a first direction when the strap is linearly expanding during inhalation and may bend in a second direction, for example outward, generating electrical current in a second, different direction when the strap is linearly contracting during exhalation. The digital electrical output of sensor 14 may be in the direction of the generated electrical current, or other digital forms, providing a digital command output indicative of whether the strap 12 is contracting or expanding. The sensor 14 can be designed to be removable from strap 12, allowing replacement of the sensor if needed.

A spring-loaded mechanism sensor, as another example, senses linear expansion and contraction of strap 12, which maybe converted to linear electrical output indicative of such linear expansion and contraction. An illustrative spring-loaded mechanism sensor includes a first element firmly connected to strap 12 close to one end thereof and a second element firmly connected to strap 12 close to the other end thereof via a non-extendable wire slidably attached to the strap. The first and second elements, which are connected by a spring, are in close proximity to each other and move relative to each other in a first direction when the user's respiratory muscles are expanding during inhalation, and in a second, opposite direction when the user's respiratory muscles are contracting during exhalation. An electrical output generating device, such as an adjustable resistor, connected to the first and second elements generates electrical output indicative of the distance or spacing between the first and second elements and/or the direction of movement of the first and/or second elements.

Figure 4:
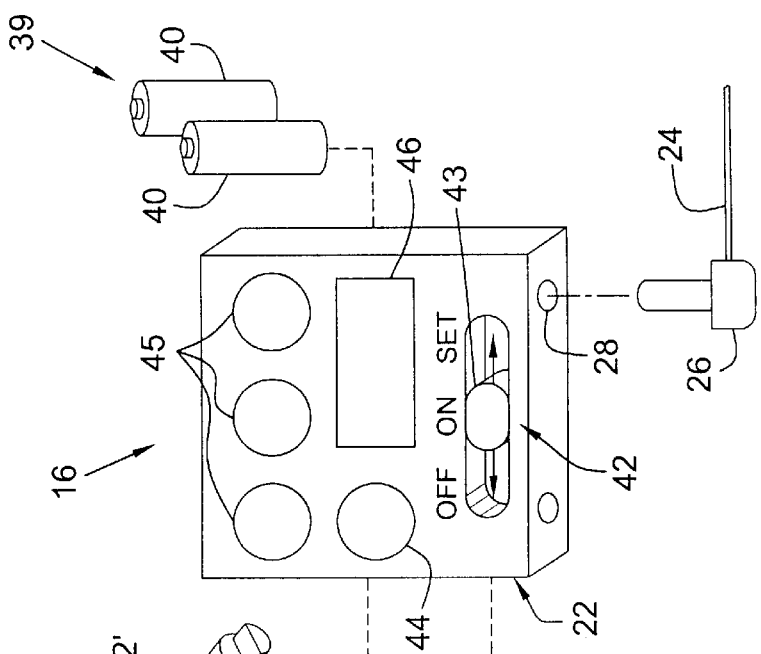
FIG. 4 is a partially exploded, front perspective view of a control unit for the indicating apparatus.

Control unit 16 is best illustrated in FIG. 4 and includes an enclosure or housing 22 mounted on strap 12, typically in proximity to sensor 14 to simplify electrical connections, such as wiring 24, between the control unit and the sensor. The control unit 16 may be removably mounted on strap 12 for removal and replacement, and may be mounted on strap 12 externally or internally, such as within a pocket of strap 12. Wiring 24, which is disposed external of strap 12, has a plug-in type electrical connector 26 at one end thereof for being removably engaged with an electrical connector 28 of control unit 16 to establish electrical communication between the sensor 14 and a processor, which is shown in FIG. 4 as a microprocessor 30, of control unit 16. The other end of wiring 24 may be hard-wired to sensor 14 or may include a suitable electrical connector for being removably engaged in a complementary electrical connector of sensor 14. The electrical connectors of wiring 24 may be male or female, the electrical connector 26 being illustrated as a male connector matingly engageable with electrical connector 28, which is illustrated as a female connector. Although wiring 24 is illustrated external of strap 12, it should be appreciated that wiring 24 may be disposed within strap 12 and provided as an internal component. Wiring 24 may include one or more wires or electrical connections depending on the electrical connections required between the sensor and the control unit. For example, in addition to being wired to the microprocessor, the sensor may be wired to a power supply for indicating apparatus 10 where the sensor is of a type requiring electric power to operate.

If linear electrical output is generated by sensor 14, microprocessor 30, which is disposed in enclosure 22, processes the linear electrical output of sensor 14 to determine whether the user is inhaling (inspiration phase) or exhaling (expiration phase) and generates a digital command output to a signaling device 32 of indicating apparatus 10. Microprocessor 30 may include a timer 34, memory 36 and a central processing unit 38 for computing desired functions, as shown in dotted lines in FIG. 4, and/or may include analog-to-digital conversion. The digital command output includes a first digital command signal generated when the microprocessor determines that the user is inhaling, i.e. that strap 12 is linearly expanding, and a second digital command signal generated when the microprocessor determines that the user is exhaling, i.e. that strap 12 is linearly contracting. Microprocessor 30 controls operation of signaling device 32, which is shown as a micro-motor 33, in response to the digital command output. When the first command signal is generated, the microprocessor 30 effects deactivation of the micro-motor 33, and the micro-motor will remain deactivated until the second command signal is generated by the microprocessor 30. When the second command signal is generated, the microprocessor 30 effects activation of the micro-motor 33, and the micro-motor 33 will remain activated until the first command signal is generated.

If sensor 14 produces digital electrical output, such digital electrical output includes first and second digital command signals generated by the sensor and used to effect deactivation and activation of the micro-motor 33 or other signaling device without the need of the microprocessor.

The micro-motor 33 is a vibratory micro-motor capable of generating or producing a sensible or perceptible tactile vibration that is tactilely sensed or felt by the user when the micro-motor is in the activated state, without generating any significant audible noise. The vibration emanating from the micro-motor 33 in the activated state is indicative of the expiration phase, and may be considered a vocalization or speak signal which serves to prompt, stimulate or cue the user to speak so that speaking may be self-synchronized with expiration. In the deactivated state, the vibration ceases, and the cessation, termination or absence of the vibration serves as another sensible or perceptible tactile signal for the user indicative of the inspiration phase. The signal produced when the micro-motor 33 is in the deactivated state may be considered a pause signal, which serves to prompt, stimulate or cue the user to inhale and pause from speaking. In this manner, pauses between speaking may be self-synchronized with inhalation or inspiration.

It should be appreciated that the micro-motor 33 may be operated to produce a vibration in response to the second command signal and to produce no vibration in response to the first command signal so that the absence of vibration serves as the vocalization signal while a sensible vibration serves as the pause signal. It should also be understood that the micro-motor 33 may be designed or operated to generate a vibration in the deactivated state that is perceptibly different or distinguishable from the vibration generated by the micro-motor in the activated state. For example, the micro-motor 33 may be operated to generate vibrations of different frequencies providing perceptibly distinguishable or different tactile sensations, respectively, to the user. Accordingly, the vocalization signal may correspond to a first vibration generated when the micro-motor 33 is in the activated state, and the pause signal may correspond to a second, different vibration generated when the micro-motor is in the deactivated state.

The indicating apparatus 10 may include more than one signaling device 32, as shown by additional signalizing device 32', which is shown as a vibratory micro-motor 33'. The micro-motor 33 may be activated by the sensor 14 or by the microprocessor 30 to generate a sensible vibration in response to the first (or second) command signal, while the micro-motor 33' may be activated by the sensor 14 or by the microprocessor to generate a perceptibly different sensible vibration in response to the second (or first) command signal. Accordingly, the vocalization and pause signals may include different vibrations, respectively, generated by the same signaling device or by different signaling devices. The one or more signaling devices can be removably disposed in the enclosure 22, which can be provided with a suitable access door or panel allowing access to the interior thereof, to permit removal and replacement. Of course, the one or more signaling devices could be mounted on strap 12 at a location remote from enclosure 22. From the foregoing, it should be appreciated that one of the vocalization signal or pause signal maybe an active signal, i.e. a vibration or other positive stimulus, while the other of the vocalization signal or pause signal is a passive signal, i.e. the absence of a vibration or other passive stimulus, or that both the vocalization and pause signals can be active signals. In a preferred embodiment, the vocalization signal is an active signal and the pause signal is a passive signal.

The power supply 39 for indicating apparatus 10 includes one or more batteries 40 mounted within enclosure 22; however, the power supply 39 can be mounted on strap 12 independently of the control unit 16 and enclosure 22. The power supply 39 is preferably removably mounted to facilitate replacement. The power supply 39, which can be rechargeable, is adapted to supply electrical power to operate the one or more micro-motors 33, 33'. The power supply can also be used to electrify or power the sensor and/or microprocessor, if needed, and to power auxiliary elements such as switches, indicators, etc.

Operation of the indicating apparatus 10 is controlled via a selection switch 42 of control unit 16, the selection switch including a sliding knob or button 43 selectively movable to "on", "off" and "set" positions. The control unit 16 may be provided with a mode selection button or dial 44, a plurality of setting pushbuttons 45, and/or an LCD display 46. While the selection switch 42 is in the "set" position, the user can input, using the setting pushbuttons 45, personal desired parameters such as minimum and/or maximum extension points for strap contraction and expansion, respectively, timing, speed and/or type of tactile signal/signals desired. The mode selection button or dial 44 allows the user to select from among several operational modes of the indicating apparatus 10. In addition to the basic synchronization mode, other operational modes may include a control mode, in which the user can control exhalation and inhalation speed (rates) and thus affect breathing cycle frequency, and an alarm mode, in which the tactile signals are produced in response to pre-set minimum and maximum extension points and/or timing parameters. The LCD display 46 provides visual presentation of setting options and/or performance of the indicating apparatus 10. The LCD display could be pivotally mounted on enclosure 22, allowing the user to see and use it while wearing the indicating apparatus.

Figure 5:
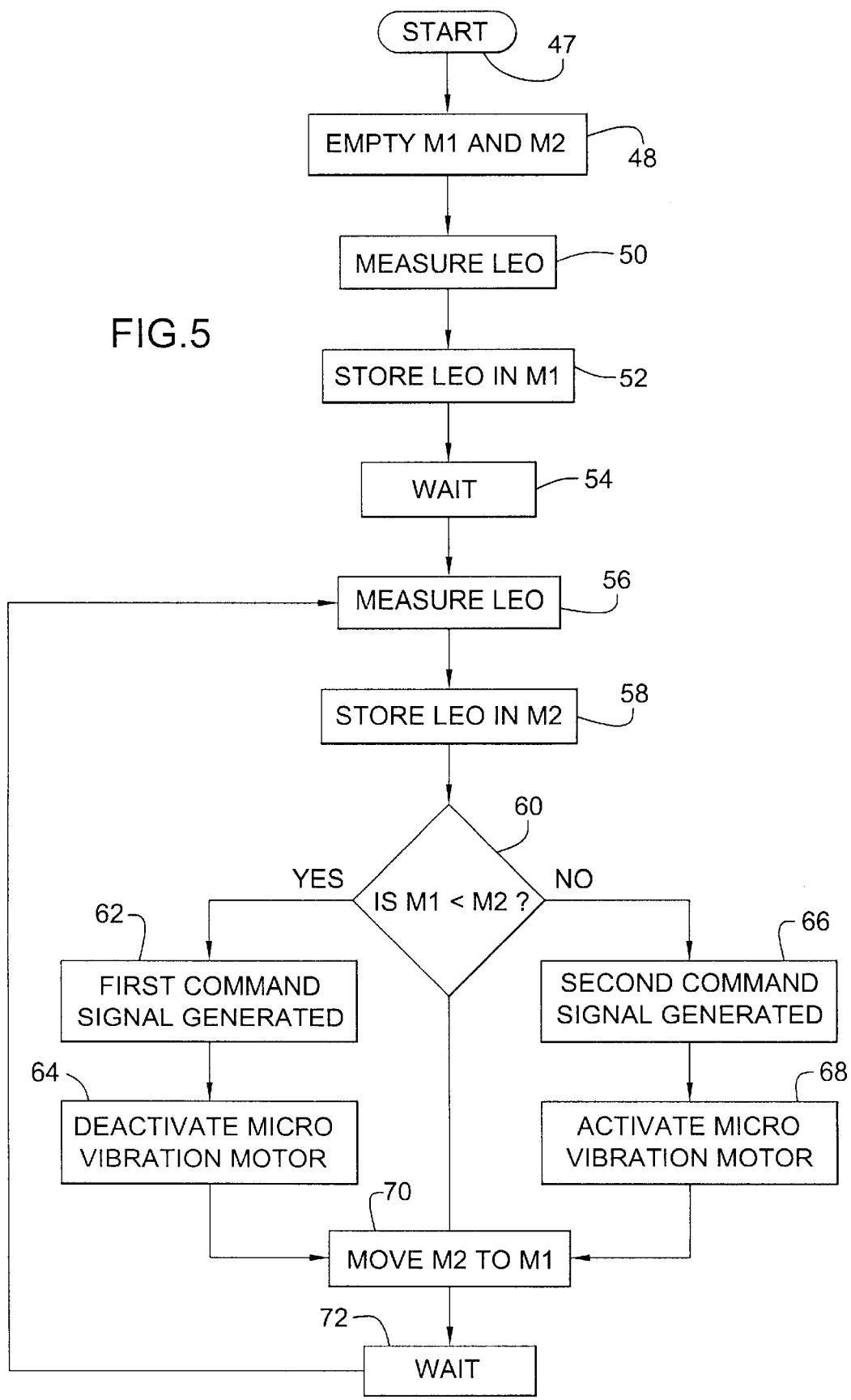
FIG. 5 is a flow diagram illustrating operation of a processor for the indicating apparatus.

FIG. 5 depicts one manner in which the microprocessor 30 can operate to control production or generation of the vocalization and pause signals over a plurality of respiratory cycles. The indicating apparatus 10 is turned "on" when the selection knob 43 of switch 42 is placed in the "on" position so that the microprocessor 30 is in a "start" mode as represented by step 47. The memory 36 of microprocessor 30 has memory slots at M1 and M2, which are initially vacated or emptied as represented by step 48. The sensor 14 senses or detects the linear condition of strap 12 and generates linear electrical output (LEO) indicative of the sensed linear condition. The microprocessor 30 measures or assigns a value to the linear electrical output generated by the sensor 14 at the beginning of an initial or first sensing interval as represented by step 50. The measurement or value assigned by microprocessor 30 to this linear electrical output is stored in memory slot M1 as represented by step 52. The sensing interval, for example 50 milliseconds, is allowed to pass as shown by the "wait" step 54. At the beginning of the next sensing interval, the microprocessor 30 again measures or assigns a value to the linear electrical output of sensor 14, as represented by step 56. The newly measured linear electrical output is stored in memory slot M2 as shown by step 58. Thereafter, microprocessor 30 determines whether the linear electrical output stored in memory slot M1 is less than the linear electrical output stored in memory slot M2 as represented in step 60. If the linear electrical output in memory slot M1 is less than the linear electrical output in memory slot M2, the microprocessor 30 generates the first command signal as shown by step 62. Generation of the first command signal effects deactivation of micro-motor 33 as shown by step 64, thereby resulting in the pause signal. Where the linear electrical output stored in memory slot M1 is not less than the linear electrical output stored in memory slot M2, the second command signal is generated by microprocessor 30 as depicted in step 66. Generation of the second command signal results in activation of the micro-motor 33, as shown by step 68, thereby resulting in the vocalization signal. Following either of steps 64 or 68, the memory slot M1 is vacated, and the linear electrical output of memory slot M2 is moved to memory slot M1, as represented by step 70, thereby opening memory slot M2 to receive the next measurement or value assigned by the microprocessor to the linear electrical output of sensor 14. As shown by "wait" step 72, the sensing interval is allowed to pass. At the beginning of the next sensing interval, step 56 is repeated so that the microprocessor 30 again measures or values the linear electrical output of sensor 14; and, thereafter, steps 57–72 are repeated. By repeating steps 56–72 so that each new linear electrical output is compared to the previous linear electrical output to obtain the appropriate command signal for deactivating or activating the micro-motor 33.

Figure 6A:
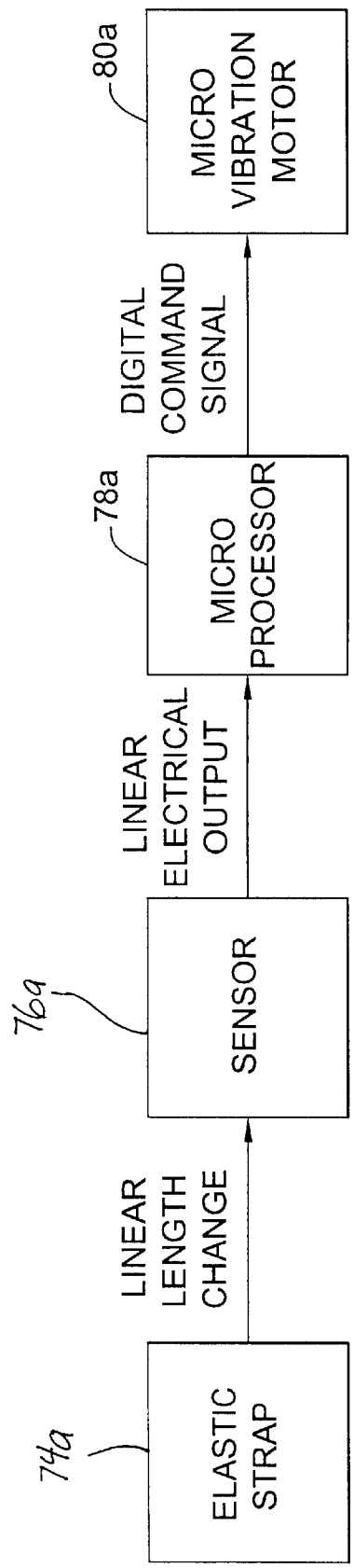
FIG. 6a is a flow diagram illustrating an indicating method according to the present invention.

A method of indicating respiratory phases according to the present invention is illustrated in FIG. 6a. The strap 12 is secured around the chest or abdomen of the user as represented by step 74a. Strap 12 can be disposed under or over clothing, but preferably is worn underneath the clothing of the user so that it may be completely hidden from view. The user may go about normal, routine activities while wearing the strap 12 and while engaging in self-synchronization of speech and respiration as made possible by the indicating apparatus 10. The sensor 14 senses the linear condition or some other variable condition of strap 12 as the user breaths, as represented by step 76a, and generates linear electrical output indicative of the sensed linear or other variable condition. The linear electrical output of sensor 14 is processed by microprocessor 30 as shown by step 78a. In particular, the microprocessor 30 determines from the linear electrical output whether the user is inhaling or exhaling, for example by determining whether the strap is linearly expanding or linearly contracting. The microprocessor 30 generates a digital command output including a first command signal which is generated when the microprocessor determines that the user is inhaling, i.e. when the microprocessor determines that the strap 12 is linearly expanding, or a second command signal generated when the microprocessor determines that the user is exhaling, i.e. when the microprocessor determines that the strap 12 is linearly contracting. The digital command output of the microprocessor 30 is used to operate the one or more micro-motors 33, 33' as shown by step 80a. Where the first command signal is generated, the one or more micro-motors are deactivated so as to produce an inaudible, tactile pause signal to the user. Where the second command signal is generated, the one or more micro-motors are activated so as to produce an inaudible, tactile vocalization signal that is perceptibly distinguishable by the user from the pause signal. Over a plurality of respiratory cycles, the user is continuously made aware of the respiratory phase currently being experienced, and is prompted or stimulated to synchronize speaking with the expiration phases and pauses in speaking with the inspiration phases of the respiratory cycles.

Figure 6B:
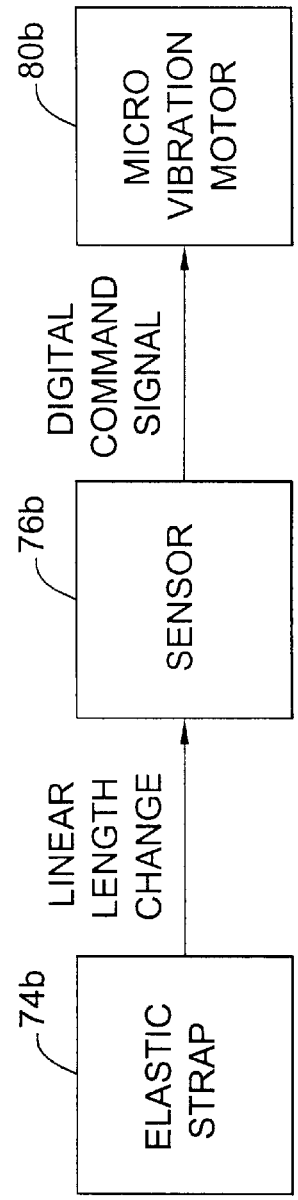
FIG. 6b is a flow diagram illustrating an alternative indicating method according to the present invention.

An alternative method of indicating respiratory phases according to the present invention is illustrated in FIG. 6b. The method illustrated in FIG. 6b is similar to that illustrated in FIG. 6a except that digital electrical output of sensor 14 defines the digital command output used to operate the one or more micro-motors 33, 33' without the use of a microprocessor. The method shown in FIG. 6b includes step 74b, which is the same as step 74a. Once the strap 12 is secured around the chest or abdomen of the user in step 74b, sensor 14 senses the linear condition or some other variable condition of strap 12 as the user breaths, and generates digital electrical output indicative of the sensed linear or other variable condition as represented by step 76b. The digital electrical output of sensor 14 includes a first command signal generated when the strap is linearly expanding, i.e. when the user is inhaling, and a second command signal generated when the strap is linearly contracting, i.e. when the user is exhaling. The digital electrical output of the sensor operates the one or more micro-motors 33, 33' in step 80b, which is the same as step 80a.

Figure 7:
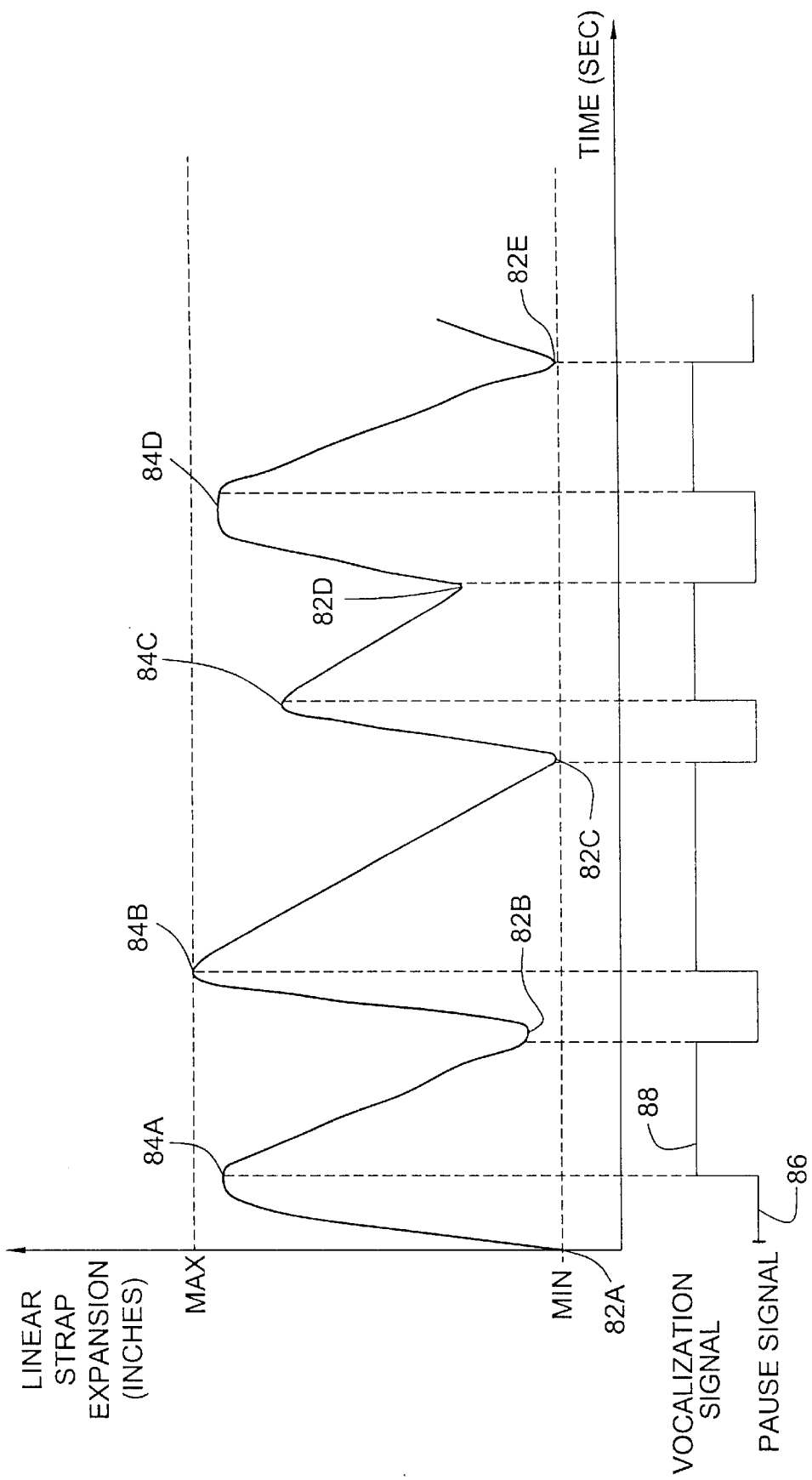
FIG. 7 graphically illustrates generation of vocalization and pause signals by the indicating apparatus in relation to movement of the strap between the contracted and expanded conditions for a plurality of respiratory cycles.

FIG. 7 graphically depicts the changes in linear condition of strap 12, as measured by linear expansion of strap 12 in inches, in relation to time, as measured in seconds, over a plurality of respiratory cycles. The change in linear condition graphically depicted in FIG. 7 is representative of the linear conditions sensed by sensor 14 over the plurality of respiratory cycles. The vertical axis (linear expansion in inches) and the horizontal axis (time in seconds) are not scaled, since specific values for inches and seconds are not essential to an understanding of the relationship depicted. Linear expansion of the strap in inches may represent total linear expansion of the strap from the relaxed condition or from any other suitable reference point. It can be seen that strap 12 is linearly expanded some amount in the contracted conditions as represented by points 82A, 82B, 82C, 82D and 82E. Point 82A represents the minimum contracted length, and point 82D represents the maximum contracted length of strap 12 for the respiratory cycles illustrated. Points 84A, 84B, 84C and 84D represent the expanded conditions for strap 12, with point 84B representing the maximum expanded length and point 84C representing the minimum expanded length for the respiratory cycles illustrated. Four respiratory cycles are illustrated in FIG. 7, each comprising an inspiration phase during which linear expansion of strap 12 increases from the contracted condition to the expanded condition and an expiration phase during which linear expansion of strap 12 decreases from the expanded condition to the contracted condition. It can be seen from FIG. 7 that the duration or length of time for the inspiration and expiration phases may vary for each respiratory cycle. The relationship between the command signals and the respiratory phases is also depicted in FIG. 7, which illustrates the presence of the pause signal 86 during each inspiration phase and the presence of vocalization signal 88 during each expiration phase. It can be seen that the pause signal 86 is in effect while the strap 12 is moved from the contracted condition to the expanded condition and that the vocalization signal is in effect while the strap 12 is moved from the expanded condition to the contracted condition.

With the indicating apparatus and methods of the present invention, inspiration and expiration respiratory phases in a user are continuously detected over a desired number of respiratory cycles, and tactilely sensible signals are provided to the user indicative of the respiratory phase currently being experienced. The signals provided to the user are silent, in that they are not audibly apparent. Each signal continues as long as the corresponding respiratory phase, so that the user is always aware of his/her current respiratory phase. The signals assist the user in self-synchronizing speech with respiration by serving as a prompt for the user to speak or vocalize during the expiration phases and to inhale and pause between speaking during the inspiration phases. The indicating apparatus and methods are embodied in a portable strap which may be inconspicuously worn by the user without the need for any cumbersome, extraneous equipment. The indicating apparatus may, however, be designed for selective connection with a computer or video monitor for home or clinical use. Because the indicating apparatus and methods do not require any cumbersome, non-portable equipment, the present invention allows individuals to practice and train speech/breathing synchrony in a non-clinical, real-time environment. Consequently, individuals are presented with more frequent opportunities for speech practice and training with correspondingly greater improvement in speech/respiration synchronization. Moreover, speech practice and training may be self-conducted in diverse real-life situations, thereby providing the user with a more meaningful practice experience.

The strap or belt may be designed in any way and/or of any suitable material to have a variable or changeable condition, i.e. a condition that varies or changes in response to inhalation and exhalation by a user wearing the strap. The variable condition can be any type of condition that undergoes change during inhalation and exhalation including, but not limited to, length and tension. The sensor can be designed in any way to sense, measure or detect the variable condition of the strap during respiration. The sensor or the processor can operate in many various ways to determine, from the variable condition that is sensed, measured or detected by the sensor, whether the user is inhaling or exhaling. For example, the processor may utilize any type of algorithm, averaging technique, etc, with or without the use of sensing intervals. The processor can be any type of electrical, mechanical or other device capable of processing, converting or transforming the output of the sensor into a form suitable for operating the signaling device. Where the output of the sensor itself is capable of operating the signaling device, a separate processor is not needed. Where a separate processor is provided, it could be incorporated on or in the sensor. The signaling device can include a motor or any other device capable of producing a tactile signal that can be felt by the user without generation of any significant sound.

Inasmuch as the present invention is subject to various modifications and changes in detail, the above description of preferred embodiments is intended to be explanatory only and not limiting. It is believed that other modifications, variations and changes will be suggested to those skilled in the art in view of the teachings set forth herein. It is therefore to be understood that all said variations, modifications and changes are believed to fall within the scope of the present invention as defined by the appended claims.

What is claimed is:

1. An indicating apparatus for indicating phases of a respiratory cycle of a user to aid in self-synchronization of speech and respiration, said apparatus comprising:

a strap adapted to be secured around the chest or abdomen of the user, said strap having a variable condition that changes as the user inhales air during inspiration phases of the respiratory cycle and as the user exhales air during expiration phases of the respiratory cycle, said strap including a sensor sensing said variable condition during the respiratory cycle said sensor generating electrical output indicative of said variable condition during the inspiration phases and during the expiration phases; and a signaling device carried by said strap and operating in response to said electrical output, said signaling device, responsive to said electrical output indicating that the respiration cycle of the user is currently in the inspiration phase, producing a first tactilely sensible condition that can be felt by the user indicative of the inspiration phase, and said signaling device, responsive to said electrical output indicating that the respiration cycle of the user is currently in the expiration phase, producing a second tactilely sensible condition that can be felt by the user indicative of the expiration phase, said second tactilely sensible condition being tactilely distinguishable from said first tactilely sensible condition.

2. The indicating apparatus as recited in claim 1 wherein said strap has opposing free ends and further including fasteners on said free ends by which said strap is adjustably secured around the chest or abdomen of the user.

3. The indicating apparatus as recited in claim 1 wherein said sensor includes a piezoelectric film element.

4. The indicating apparatus as recited in claim 1 wherein said sensor includes a spring-loaded mechanism.

5. The indicating apparatus as recited in claim 1 wherein said sensor includes a resistive flexible member.

6. The indicating apparatus as recited in claim 1 wherein said variable condition is tension in said strap.

7. The indicating apparatus as recited in claim 1 wherein said electrical output is digital electrical output.

8. The indicating apparatus as recited in claim 7 wherein said digital electrical output includes a first digital command signal generated by said sensor during the inspiration phase and a second digital command signal generated by said sensor during the expiration phase, the tactilely sensible conditions of said signaling device being activation and deactivation of a tactile stimulus that can be felt by the user, said signaling device being deactivated in response to said first digital command signal and being activated in response to said second digital command signal.

9. The indicating apparatus as recited in claim 1 wherein said electrical output is electrical output indicating a varying magnitude of the variable condition.

10. The indicating apparatus as recited in claim 9 and further including a processor carried by said strap, said processor processing said electrical output to determine whether the user is in the inspiration phase or the expiration phase, said processor generating a first digital command signal in response to a determination that the user is inhaling and generating a second digital command signal in response to a determination that the user is exhaling, said signaling device producing the first tactilely sensible condition in response to said first digital command signal and producing the second tactilely sensible condition in response to said second digital command signal.

11. The indicating apparatus as recited in claim 1 and further including a power supply mounted on said strap for supplying electric power to said signaling device.

12. The indicating apparatus as recited in claim 1 wherein said signaling device includes a vibratory motor, one of said first or second tactilely sensible conditions is the absence of a perceptible vibration emanating from said motor and the other of said first or second tactilely sensible conditions is a perceptible vibration emanating from said motor.

13. The indicating apparatus as recited in claim 12 wherein said first tactilely sensible condition is the absence of the perceptible vibration emanating from said motor and said second tactilely sensible condition is the perceptible vibration emanating from said motor.

14. The indicating apparatus as recited in claim 1 and further including a control unit on said strap for selectively controlling operational parameters of said indicating apparatus.

15. An indicating apparatus aiding in self-synchronization of speech and respiration in a user, said apparatus comprising
a stretchable strap for being secured around the chest or abdomen of the user, said strap expanding linearly in response to expansion of the chest or abdomen when the user inhales air during respiration and contracting linearly in response to contraction of the chest or abdomen when the user exhales air during respiration, said strap having a sensor sensing linear expansions and contractions of said strap, said sensor producing time-varying electrical output indicative of the sensed linear expansions and contractions;
a processor carried by said strap, said processor processing said electrical output to generate a first command signal when said electrical output indicates that said strap is currently expanding and a second command signal when said electrical output indicates that said strap is currently contracting; and
a vibrating device carried by said strap and operating responsive to said first and second command signals, said vibrating device operating responsive to said first command signal so as to produce a tactilely perceptible pause signal prompting the user to pause from speaking, said vibrating device operating responsive to said second command signal to produce a tactilely perceptible vocalization signal prompting the user to speak.

16. The indicating apparatus as recited in claim 15 wherein said processor includes a central processing unit, memory and a timer.

17. The indicating apparatus of claim 15, wherein said vibrating device selectively produces vibration that can be felt by the user, and wherein one of said vocalization and pause signals is a presence of the vibration, and the other of said vocalization and pause signals is an absence of the vibration.

18. A method of self-synchronizing speech with respiration, said method comprising the steps of:
wearing a stretchable strap of an indicating apparatus so that the strap linearly expands in response to expansion of the respiratory muscles during the inspiration phase of a respiratory cycle and linearly contracts in response to contraction of the respiratory muscles during the expiration phase of the respiratory cycle;
perceiving a tactile vocalization signal produced by the indicating apparatus while the strap is linearly contracting in the expiration phase;
speaking while perceiving the tactile vocalization signal;
perceiving a tactile pause signal produced by the indicating apparatus while the strap is linearly expanding in the inspiration phase;
inhaling air and pausing from speaking while perceiving the tactile pause signal; and
repeating said step of perceiving a tactile vocalization signal, said step of speaking, said step of perceiving a tactile pause signal and said step of inhaling air and pausing for a plurality of respiratory cycles so as to synchronize speaking with the expiration phases and to synchronize pauses in speaking with the inspiration phases.

19. The method of claim 18, wherein the vocalization signal is vibration of a device in contact with the user, and the pause signal is absence of said vibration.

20. The method of self-synchronizing speech with respiration as recited in claim 18 wherein said step of wearing includes wearing the strap over the respiratory muscles.

21. An indicating apparatus for indicating respiratory phases in a user to permit self-synchronization of speech and respiration, said apparatus comprising:

strap means removably securable around the chest or abdomen of the user and being capable of linearly expanding and linearly contracting in response to expansion and contraction of the chest or abdomen as the user inhales and exhales air, respectively, said strap means having sensing means for sensing the linear condition of said strap means as the user inhales and exhales;

processor means carried on said strap means for measuring the linear condition sensed by said sensing means and determining whether said strap means is linearly expanding or linearly contracting, said processor means generating a first command signal in response to a determination that said strap means is linearly expanding and generating a second command signal in response to a determination that said strap means is linearly contracting; and signaling means carried on said strap means for producing tactilely sensible signals, said signaling means being controlled by said command signals to produce a tactilely sensible pause signal when said first command signal is generated and to produce a tactilely sensible vocalization signal when said second command signal is generated, whereby said pause signal begins coincident with detection of respiratory inspiration so as to prompt the user to refrain from speaking during inhalation of air, and said vocalization signal begins coincident with detection of respiratory expiration so as to prompt the user to speak during exhalation of air.

22. The indicating apparatus of claim 21 wherein said signaling means is a vibrational device selectively vibrates responsive to one of the command signals so as to be felt by the user, and does not vibrate responsive to the other of the command signals.

23. A method of indicating respiratory phases in a user, said method comprising the steps of:

sensing a variable condition of a strap that is worn around the chest or abdomen of the user as the variable condition changes in response to expansion and contraction of the chest or abdomen during inhalation and exhalation, respectively;

generating electrical output indicating the variable condition during inhalation and exhalation;

determining from a most recent of said electrical output whether the user is in an exhalation phase of respiration; and producing, responsive to a determination that the user is currently in an exhalation phase, a first tactilely sensible condition that can be felt by the user; and producing, responsive to a determination that the user is currently not in an exhalation phase, a second tactilely sensible condition that can be felt by the user and that is tactilely distinguishable from the first condition.

24. The method of claim 23 the variable condition is the sensed circumference of the chest or abdomen of the user from the strap extending therearound.

25. The method of claim 24 wherein said sensing, determining, and producing of said tactilely sensible conditions is performed in a portable apparatus supported on the body of the user.

26. The method of claim 25 wherein the determining of the exhalation phase is based on the most recent output indicting that the strap is contracting in circumferential length.

27. The method of claim 23 wherein one of the tactically sensible conditions is a presence of vibration in a device in contact with the user, and the other tactically sensible condition is absence of said vibration.

28. A portable apparatus for aiding a user in synchronizing speech with exhalation phases of a respiratory cycle of the user, said apparatus comprising:

a sensing apparatus carried on the chest or abdomen of the user, said sensing apparatus detecting a varying physical parameter of the user indicative of degree of expansion of the chest or abdomen of the user during the user's respiratory cycle and transmitting a varying signal derived from said detected physical parameter;

a processor receiving the signal from the sensing apparatus, and a signal device controlled by the processor and configured to give a tactile signal to the user, said processor determining whether said signal indicates that the user is currently in an exhalation phase, and said processor, responsive to said determination that the user is currently in an exhalation phase, causing said signal device to impart to the user the tactile signal.

29. The apparatus of claim 28, wherein the physical parameter from which the sensing apparatus derives the signal is a circumference of the chest or abdomen of the user.

30. The apparatus of claim 28, wherein the sensing apparatus includes a strap adapted to be secured about the chest or abdomen of the user, and an electronic device generating the signal varying dependent on expansion or contraction of said strap as the user inhales and exhales.

31. The apparatus of claim 30, wherein the signal is a series of digital readings of varying circumferences of the strap.

32. The apparatus of claim 28, wherein the signal device signals the user by vibrating during the exhalation phase.

33. The apparatus of claim 28 wherein, during the exhalation phase, the signal device signals the user by discontinuing the vibration.

34. The apparatus of claim 28 wherein the signal device continuously detects the varying physical parameter of the user.

* * * * *